United States Patent [19]

Harrington et al.

[11] Patent Number: 5,637,202
[45] Date of Patent: Jun. 10, 1997

[54] POROUS ELECTROPHORESIS SPONGES

[75] Inventors: Michael G. Harrington, La Canada, Calif.; Kelvin H. Lee, Williamsville, N.Y.

[73] Assignee: California Institute of Technology, Pasadena, Calif.

[21] Appl. No.: 400,666

[22] Filed: Mar. 8, 1995

Related U.S. Application Data

[63] Continuation of Ser. No. 144,129, Oct. 27, 1993, abandoned.
[51] Int. Cl.$^6$ ............................................. C25B 9/00
[52] U.S. Cl. .................. 204/469; 204/606; 204/616; 252/315.1
[58] Field of Search ................. 204/299 R, 182.8, 204/606, 616, 469; 252/315.1

[56] References Cited

U.S. PATENT DOCUMENTS

| | | | |
|---|---|---|---|
| 4,128,470 | 12/1978 | Hiratsuka et al. | 204/299 R |
| 4,704,198 | 11/1987 | Ebersole et al. | 204/182.8 |
| 4,790,919 | 12/1988 | Baylor, Jr. | 204/182.8 |
| 5,019,232 | 5/1991 | Wilson et al. | 204/182.8 |
| 5,135,627 | 8/1992 | Soane | 204/299 R |
| 5,164,057 | 11/1992 | Mori et al. | 204/299 R |
| 5,196,099 | 3/1993 | Mori et al. | 204/282.8 |
| 5,202,007 | 4/1993 | Kuzulic | 204/182.8 |
| 5,290,411 | 3/1994 | Zerwert et al. | 204/182.8 |
| 5,403,900 | 4/1995 | Wu et al. | 526/214 |
| 5,426,786 | 6/1995 | Calvin | 2/2 |

*Primary Examiner*—Howard E. Schain
*Assistant Examiner*—C. Delacroix-Muirheid
*Attorney, Agent, or Firm*—Oppenheimer Poms Smith

[57] ABSTRACT

Porous plastic electrophoresis sponges having pore sizes range from $10^{-9}$ to $10^{-3}$ meters. The sponges are made from polyethylene, polypropylene, polytetrafluoroethylene, polyvinylidine difluoride, polynitrile or polystyrene. The porous plastic sponges are commercially available and are supplied in a prefabricated form which eliminates the preparative and pouring steps required for conventional gel electrophoresis support media. The porous sponges are available in a range of pore sizes and densities for use in a variety of electrophoresis systems to separate a variety of different materials including proteins, peptides and DNA. The porous electrophoresis sponges are relatively inert and may be used with organic solvents.

13 Claims, 4 Drawing Sheets

←200μm→

POROUS ELECTROPHORESIS SPONGES

The present invention was made with the support of the National Science Foundation Grant No. DIR-8809710. The United States Government may have rights to the invention.

This is a continuation of application Ser. No. 08/144,129 filed on Oct. 27, 1993, now abandoned.

BACKGROUND OF THE INVENTION

1. Field of the Invention

The present invention relates generally to the support medias used in electrophoresis. More particularly, the present invention is directed to the use of polymer sponges as a support media.

2. Description of Related Art

Support media are commonly used in electrophoresis systems to suppress convection caused by gravity, thermal gradients or concentration gradients. The support media which have been used conventionally include powdered and porous solids, fibrous materials and gels. The powdered and porous materials which are used as electrophoresis mediums include cellulose, starch, silica, glass, polyurethane foam and glass powder. For the most part, the powdered and porous solid electrophoresis media have been replaced by gels which have a higher resolving power. The powdered and porous solids are generally reserved for large scale preparative separations.

Fibrous materials, such as paper have been used in electrophoresis for many years. Paper electrophoresis support media became popular due to their low cost and ease of handling. However, the use of paper as a support media has largely been replaced with gels due to problems experienced with variations in different batches of paper and impurities in the paper which caused undesirable and unpredictable absorptive properties.

Cellulose acetate membranes have also been used as an electrophoresis support media. Cellulose acetate membranes do not have the undesirable absorptive properties of paper and have a uniform microporous structure and are chemically inert except for a small number of charged groups that must be neutralized if isoelectric focusing is performed. However, cellulose acetate must be laminated to a flexible plastic support due to the inherent brittleness of dry cellulose acetate.

The most popular electrophoresis support materials are based on molecular-sieve gels. Starch gels were initially used in the early 1950's for the separation of proteins. However, the narrow range of porosities and the fragile nature of starch gels have rendered them obsolete. Agar and agarose gels have been widely used as an electrophoresis support media. Agar and agarose gels are obtained from polysaccharides extracted from red algae. Agar and agarose gels have not been widely used as an electrophoresis support media because of limited sieving properties and a high content of anionic residues, such as sulfate and pyruvate.

Polyacrylamide gel (PAG) has been widely adopted as the support media of choice for the separation of both proteins and DNA. Cross-linked polyacrylamide provides good resolution in many applications because it possesses chromatographic (i.e. sieving) as well as anti-convective properties. The chromatographic properties of cross-linked polyacrylamide gels are particularly well-suited for molecular weight separations. By varying the percentage of monomer or cross-linker, the nature of the gel can be changed to suit a variety of separations from small (1,000 kD) peptides to large (500,000 kD) proteins.

Despite the numerous advantages and popularity of polyacrylamide gel support media, there are a number of inconveniences, hazards and limitations which accompany the use of this material. For example, the acrylamide monomer and the bis-acrylamide cross-linker represent a serious health hazard. Although the polymer is not toxic, exposure to the monomer and cross-linker during preparation of the gel poses significant health concerns. In addition, residual and derivative chemicals present during post-electrophoresis processing also pose health concerns.

The health problems associated with acrylamide monomer are compounded by the fact that the toxic effects of acrylamide are cumulative. The toxicity problem associated with acrylamide monomers can be carefully controlled in a research setting. However, toxicity concerns seriously limit the use of polyacrylamide gel in clinical settings where people being exposed to the toxins may not be well-informed about the risks associated with acrylamide monomer and carefully trained with respect to proper handling procedures.

Another problem associated with polyacrylamide gel support media is the difficulty in forming gels of reproducible properties. Acrylamide monomers and the bis-acrylamide cross-linkers are commercially available as extremely pure and uniform compositions. However, preparation of the electrophoresis support media involves a high degree of skill and care. Slight changes in preparation technique from batch to batch results in the formation of gels having slightly different properties. Further, the pouring process for preparation of the gel is prone to minor variations which result in the formation of gels which vary in composition at different locations within the gel.

A number of manufacturers sell pre-cast polyacrylamide gels that have been at least partially accepted by users. These provide simplicity to the users who do not need to cast the gels, but all other limitations of polyacrylamide gels remain.

The variability present in polyacrylamide gel support media results in inconsistent protein migration within a particular gel media. Further, protein migration is not reproducible when different batches of gel are used. As a result of these inconsistencies, polyacrylamide gel support media has not been widely used in clinical applications. Instead, cellulose acetate membranes have been used even though they have considerably less resolution power.

Two dimensional electrophoresis (2DE) is a technique which allows the identification of thousands of molecules simultaneously. In 2DE systems, the samples are subjected to electrophoresis based on two independent variables such as charge and mass. For example, in a first dimension, isoelectric focusing (IEF) is used to separate complex mixtures based on charge. In a second dimension, polyacrylamide gel electrophoresis is used to separate the samples based on mass. The resulting 2-dimensional image contains the positional coordinates and quantity of each species as well as all interconnecting correlations. Unlike a series of one-dimensional separations, the 2DE gel image provides a data base which is suitable for determining individual differences between samples and for the analysis of molecular networks.

The full potential of two-dimensional electrophoresis has been difficult to obtain because of non-uniformities in the polyacrylamide gel support media. For example, the computer matching of up to thousands of protein spots on a two-dimensional electrophoresis is greatly hindered by artifacts in the polyacrylamide gel support media such as bubbles, insoluble material, polymer concentration gradients and cross-link density variabilities. These variabilities or artifacts in the gel give rise to glitches in protein spot structure and gel-to-gel variations in composition that result in irreproducibility of relative protein or DNA migration velocities.

In view of the above problems with present electrophoresis support media, it would be desirable to provide electrophoresis support media which are non-toxic and easily handled. Further, the procedures and techniques for forming the support media should be simple and easily mastered so that uniform support media with reproducible characteristics can be prepared routinely. Even better, it would be desirable to provide support media which are ready to use when received by the technician without requiring gel pouring or other conventional fabrication steps. Finally, the properties of the support media should be such that they are suitable for use in high performance electrophoresis systems, such as two-dimensional electrophoresis.

Many times it is desirable to use organic solvents in the electrophoresis process. The present electrophoresis medias, such as polyacrylamide gel are not well-suited for use with organic solvents to separate hydrophobic molecules. Accordingly, there is also a need to provide electrophoresis support media which not only have all of the above mentioned desired characteristics, but are also suitable for use with organic solvents.

SUMMARY OF THE INVENTION

In accordance with the present invention, electrophoresis support media are provided which overcome many of the above-mentioned problems. The electrophoresis support medias of the present invention are structurally strong, non-toxic, and are particularly well-suited for use in high performance electrophoresis, such as two-dimensional electrophoresis. The medias are provided in a prefabricated form which eliminates the need for complicated preparative procedures. They can be molded or cut to any shape and are easier to handle than gels. Further, the cut sponges retain their shape and they can be re-used, if desired, and stored indefinitely.

The present invention is based upon the discovery that certain types of polymer sponges may be used as an electrophoresis support media. As a feature of the present invention, it was discovered that porous sponges made from polyethylene, polypropylene, polytetrafluoroethylene, polyvinylidine difluoride (PVDF), polynitrile and polystyrene are especially well-suited for use as electrophoresis media. The porous polymer sponge electrophoresis support media in accordance with the present invention are available commercially from various manufacturers. These commercially available porous sponges have relatively uniform pore sizes and pore distribution which make it possible to obtain accurate and reproducible electrophoresis separations.

As another feature of the present invention, the preformed polymer sponge electrophoresis support media are well-suited for use with both aqueous and organic electrophoresis solvents. The polymer sponges can range from hydrophilic to hydrophobic with capabilities ranging from inert to reactive surfaces.

As another feature of the present invention, the polymer sponges may be used to separate a variety of materials including proteins, peptides and DNA. Separation of these different materials is achieved by selecting a polymer sponge having an appropriate pore size which can range from sub-nanometer to micron (100 μm) scale. The commercially manufactured polymer sponges have pore sizes which are uniform and carefully controlled within high tolerance limits. Accordingly, high performance electrophoresis of a variety of materials can be achieved. As a further feature, the polymer sponge materials may be derivatized to provide added functionality. Also, various chemicals may be absorbed into the porous structure to enhance certain types of electrophoresis.

The polymer sponges of the present invention are easy to use, versatile, resilient, relatively inexpensive and provide separation characteristics which are equivalent to presently available gel support media. Accordingly, the polymer sponges provide an attractive alternative to conventional gel electrophoresis.

The above discussed and many other features and attendant advantages of the present invention will become better understood by reference to the following detailed description of the preferred embodiments when taken in conjunction with the accompanying drawings.

DETAILED DESCRIPTION OF THE PREFERRED EMBODIMENTS

The present invention involves the use of prefabricated polymer sponges as an electrophoresis support media. The various polymer sponges encompassed by the present invention may be used in a wide variety of electrophoresis systems as a substitute for cellulose acetate, agarose gel, agar gel, polyacrylamide gel or other conventional support media. The porous plastic materials encompassed by the present invention can be formed into layers, columns, or any of the other well-known shapes typically employed in gel electrophoresis systems.

Figure 1:
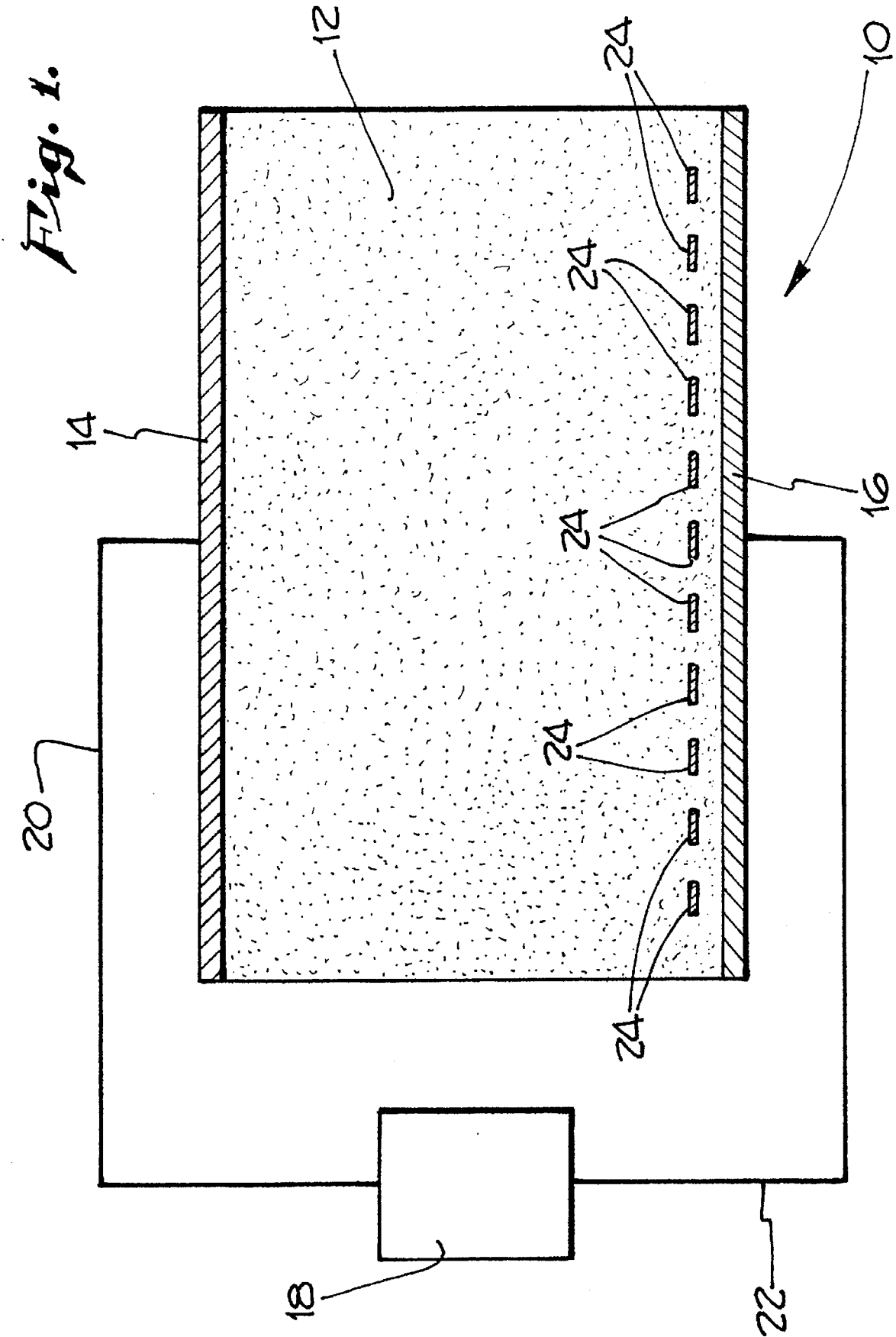
FIG. 1 is a schematic representation of an exemplary electrophoresis system utilizing a polymer sponge in accordance with the present invention.

An exemplary electrophoresis system utilizing a polymer sponge in accordance with the present invention is shown generally at 10 in FIG. 1. The system 10 includes the polymer sponge 12 which is connected on two opposite ends to electrodes 14 and 16 in the same manner as conventional gel electrophoresis. The electrodes 14 and 16 are connected to an electrophoresis power pack 18 by way of line 20 and 22, respectively. The sponge 12 and attached electrodes 14 and 16 are immersed in electrophoresis buffer and used in the same manner as other conventional electrophoresis materials. Sample wells or locations are provided in the polymer sponge 12 as shown at 24. As is well known, the various samples of interest to be separated by electrophoresis are placed at the sample locations or placed into the wells 24 using any of the standard sample introduction techniques.

The porous polymer sponges in accordance with the present invention are made from polyethylene, polypropylene, polytetrafluoroethylene, polyvinylidine difluoride, polynitrile or polystyrene. All of these polymer sponges are available commercially as porous sponges in a wide variety of shapes. Polyvinylidine difluoride obtained from Porex (Fairburn, Ga.) is a preferred porous material. Porous sponges from other manufacturers, such as Monarch Marking Systems (Dayton, Ohio) may be used. In addition, if desired, the polymer sponges may be made by polymerizing appropriate monomers according to conventional foam forming techniques. The procedures for making polymer sponges are well known and will not be described in detail. Preferably, the polymer sponges are not prepared by the electrophoresis technician. Instead, the sponges are obtained from one of the many manufacturers marketing such products.

In order for the porous polymer sponge to be useful as an electrophoresis support media, it should have pores which range in size from less than $10^{-9}$ up to $10^{-3}$ meters. For most electrophoresis applications, it is preferred that the pore size distribution be uniform throughout the polymer sponge material. However, for certain electrophoresis gradient separations, polymer sponges having pore sizes which vary gradually from one location to another may be used.

The particular pore size chosen for the sponge support media will vary depending upon the material which is to be electrophoretically separated. The appropriate pore size may be determined experimentally. In general, sponges having pore sizes which range from 1 μm to 25 μm are suitable for separating proteins having molecular weights in the range of 5,000 to 500,000. These pore sizes are of sufficient size to allow electrophoretic migration of the protein through the sponge during electrophoresis. With regards to electrophoresis of peptides having molecular weights of up to 5,000, it is preferred that sponges with sizes in the range of 0.1 μm to 10 μm be used. Pore sizes within this range are of sufficient size to allow electrophoretic migration of the peptides through the sponge during electrophoresis. Sponges having pore sizes of between about 1 μm to 100 μm are suitable for use in separating DNA and/or RNA.

The sponges in accordance with the present invention are available in a wide variety of shapes which can be used as electrophoresis support media. Preferably, the sponges will be in the shape of a layer which has a thickness of between 0.5 millimeters and 3 millimeters and a surface area of between 5 cm² and 500 cm². Sponges in the shape of a column are also well suited for many electrophoresis processes. The sponges must have an open pore structure to allow movement through the plastic of the solvents and materials being separated. The surface of the sponges must include open pores to allow entry of solvents and other materials into the body of the sponge. The ratio of the pore void volume to total sponge volume can be varied depending upon the overall size of the sponge, and size of the pores, and the particular electrophoresis being conducted and the desired media density. Preferably, the ratio of void volume to total volume will be between about 40 volume percent to 80 volume percent.

An advantage of the sponges in accordance with the present invention is that they are substantially inert and therefore not attacked by either aqueous or organic electrophoresis solvents. Any of the conventional organic solvents, such as dimethylformamide (DMF), dimethylsulfoxide (DMSO), and tetramethylurea (TMU) may be used. In addition, mixed solvents utilizing both organic and aqueous solvents may be used.

The polymer sponge support media in accordance with the present invention are used in the same manner as existing conventional electrophoresis support media. The advantage of the sponge is that it can be obtained commercially in a form which is ready to use and requires little if any preparative work by the electrophoresis technician. The sponges are durable and are easily handled. Further, if desired, the sponges may be treated chemically for added functionality to enhance the electrophoretic separation.

Examples of practice are as follows:

The following samples of porous plastic sponges from the Porex Technologies inventory were used: extra fine polyethylene (average pore size—27 μm, Pores (#4920), fine polyethylene (average pore size—69 μm, Porex #4900), medium polyethylene (average pore size—119 μm, Porex #4903), coarse polyethylene (average pore size—167 μm, Porex #4732), polypropylene (Porex #4908) and polytetrafluoroethylene. All samples were provided as 12"×12"× 1/16" sheets. Samples of 4920 and 4732 were analyzed with respect to elemental composition, pore size distribution, and by scanning electron microscopy. The elemental analysis was performed by Galbraith Laboratories, Knoxville, Tenn. The composition of the samples were consistent with the known structures.

Figure 2:
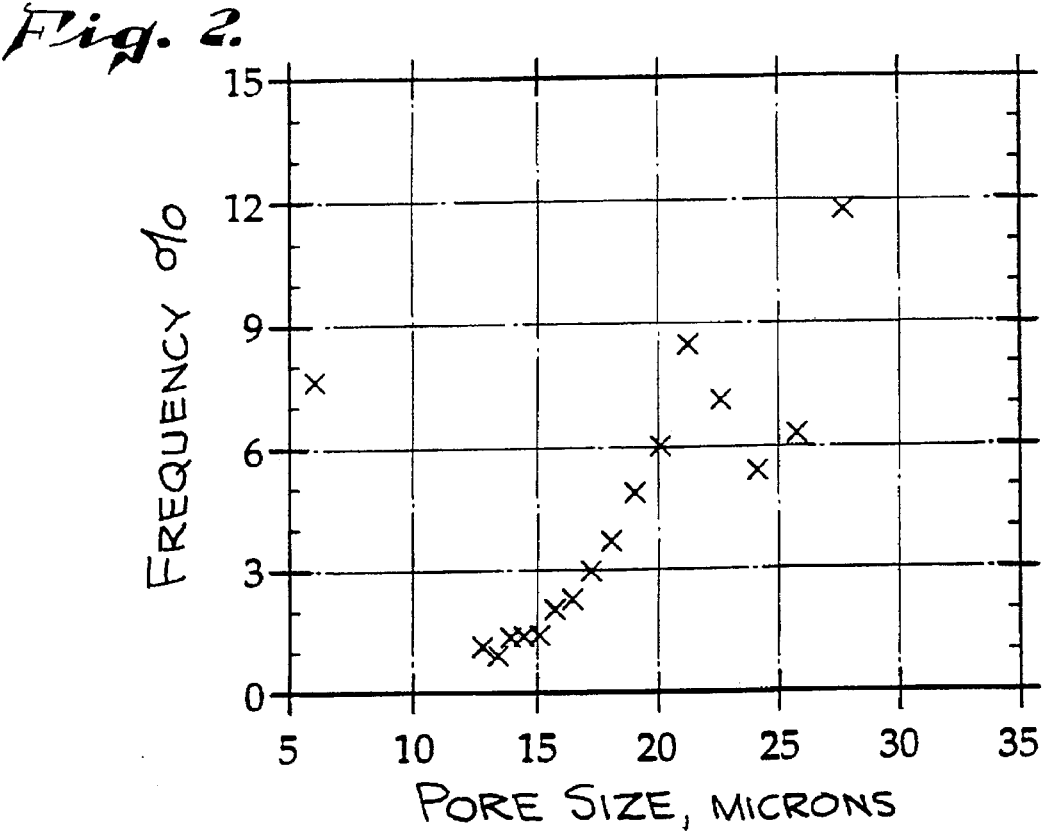
FIG. 2 is a graph showing pore size distribution for an exemplary polyethylene polymer sponge.
Figure 3:
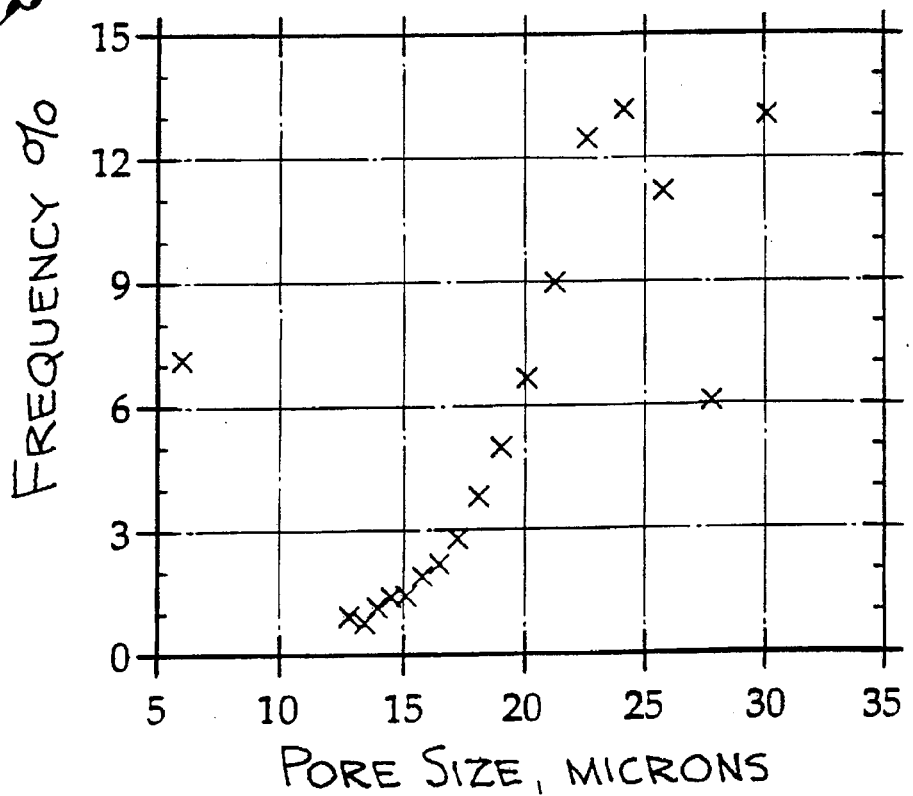
FIG. 3 is a graph showing pore size distribution for an exemplary PVDF polymer sponge.

Pore size distribution measurements of extra fine polyethylene and PVDF were performed on a Micromeretics Mercury Intrusion Porisimeter at Porex Technologies. Pore size distribution measurements of these materials are shown in FIGS. 2 and 3.

Figure 4:
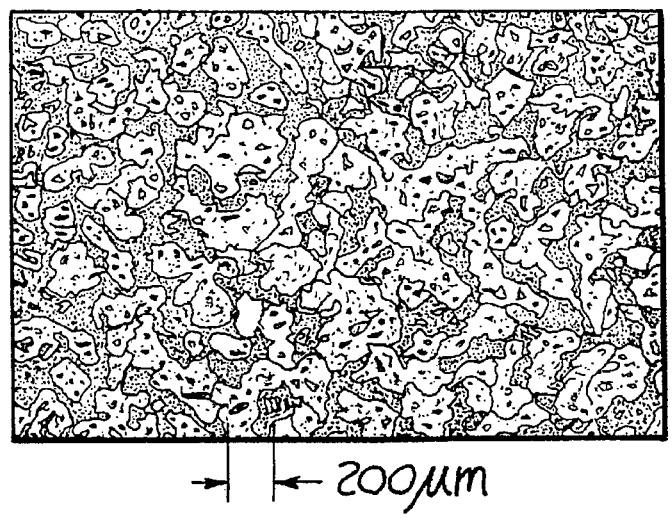
FIG. 4 is an electron micrograph of an exemplary polyethylene polymer sponge.

A representative 50× magnification scanning electron micrograph (Porex Technologies) of the pore structure of fine polyethylene, after a solution of 0.5 3-([3-cholamidopropyl)-dimethyl-ammonio]-1-propane sulfonate (CHAPS) was wicked into the plastic and dried at 60° C., is shown in FIG. 4.

Bovine serum albumin (BSA) and corn zein were prepared for electrophoresis as follows:

Bovine serum albumin (BSA) and corn zein were purchased from Sigma and soybean trypsinogen inhibitor was purchased from Boehringer Mannheim. Preliminary studies showed that with the currently tested materials, we could not fix proteins for staining using conventional cross-linking with glutaraldehyde. Therefore, to visualize proteins we employed either naturally chromogenic, or radioactively or fluorescently labeled proteins, or we stained the proteins after their transfer into a polyacrylamide 2DE gel.

5-iodoacetamide fluorescein and tetramethyl rhodamine-5-iodoacetamide (Molecular Probes, Inc.) were dissolved in dimethyl sulfoxide at 2 mg/mL. They were conjugated overnight at a five fold molar excess, to a solution of individual proteins dissolved in tris buffered saline (TBS) buffer pH 7.5 (at 10 mg/mL)+0.2% dithiothreitol (DTT). The resulting labelled protein mixtures were purified by size exclusion chromatography on Sephadex G25M columns (PD-10, Pharmacia-LKB) which were equilibrated with 3 volumes of TBS pH 7.5 buffer. The protein containing fractions were pooled and further purified and concentrated by ultrafiltration in Centricon-10 filters (Amicon, Inc.).

355-methionine labelled proteins from 48 hour embryos of the sea urchin $Strongylocentrotus$ $purpuratus$ were a gift from C. Smith. Proteins were in solution in 8M urea, 2 DTT and 2% carrier ampholytes (Bio-Rad 3-10) at a concentration of 8 mg/mL with $6.5 \times 10^5$ cpm/20 μL of TCA precipitable counts.

Human cerebral spinal fluid (CSF) was obtained from a 50-year old male with ill-defined dementia. The protein concentration of the CSF was 80 mg/mL. For electrophoresis, 20–65µL of CSF was mixed with 5 µL of a solution containing 8M urea, 2% DTT and 2% carrier ampholytes (Bio-Rad 3-10) and used for each electrophoresis run.

Isoelectric focusing (IEF) was conducted using the following protocol:

Sheets (1/16" thickness) of the porous plastic sponges were cut into 1-3/32" by 6" strips. The strips were soaked for two hours in a solution containing 9M urea, 2% carrier ampholytes, 0.5% Nonidet-P40, 2% CHAPS, and water. This is the standard IEF carrier ampholyte/polyacrylamide solution as described by Harrington, et al., *Methods: A Companion to Methods in Enzymology*, 1991, 3, 33–139, with the change that $H_2O$ was substituted for the acrylamide/crosslinker solution and no catalyst was added. 10–200 µg protein was placed onto the surface 2 cm from the basic end of the strips. The proteins were wicked into the strips.

The strips were run horizontally on top of a glass plate placed on top of an Ultra-Lum UV 365 nm transilluminator. The electrodes from a Pharmacia/LKB Multiphor II apparatus were attached to a second glass plate which was placed on top of the strips. Filter papers presoaked in 6 mM $H_3PO_4$ or 10 mM NaOH, were used to mount the electrodes onto the polymer sponge. The second glass plate and the Multiphor II cover were used to reduce evaporation. The system was powered by a BioRad 3000Xi power supply. The strips were run at varying electrical conditions, but the optimum of IEF (with the least evaporation as the main limiting factor) was 500 V for 2 hours, 1000 V for 2 hours and 1250 V to a total of 5500 Vh or until excessive drying of the strips prevented further migration from occurring. These times are about three-fold faster than that time to achieve similar separations in polyacrylamide gels. A tripod mounted 35 mm Pentax SF10 SLR camera with 50 mm Macro lens was used to record protein migration.

When IEF was performed under paraffin oil (Baker), the Pharmacia-LKB Immobiline strip tray and electrodes that accompany the Multiphor II apparatus were used in place of the two glass plates and electrodes.

The pH gradients maintained by the carrier ampholytes in the plastic sponge strips or polyacrylamide tube gels were determined by sectioning the media into 15 pieces, each 1 cm long. These pieces were soaked in deionized water for one hour and the pH was measured on a Beckman Model pHI 31 pH meter. Measurements were recorded at 1 Vh, 100 Vh, 2000 Vh, 3000 Vh, 5000 Vh, 13,000 Vh and 18,000 Vh.

For each electrophoresis run, photographs were taken every 15 to 20 minutes from the onset of voltage until focusing was achieved. The proteins were visible with the use of the UV transilluminator and photographs were made from Kodak Ektar 25 speed film at an f-stop of 2.8 and either a 1 second or ½ second exposure time (depending on ambient lighting). Measurements of protein migration were made directly from the prints.

Radio-labelled proteins were visualized on a Molecular Dynamics Series 400 PhosphorImaging system utilizing ImageQuant software. The images were transferred to a SUN 4/260 workstation running GAltool software (Solomon, et al., *CABIOS*, 1993, 9, 133–139) and printed on a Lasertechnics Model 300D continuous tone printer. Measurements of the amount of protein present were made after isoelectric focusing in the electrophoresis sponge strips or polyacrylamide tube gels and then in the strips or gels after the proteins were electrotransferred onto a second dimension SDS-PAGE gel.

The following polymers were soaked into the pores of Porex coarse polyethylene (average pore size 165 µm): 1% dextran molecular weight 100,000–200,000 (Polysciences, Inc.) in deionized water, 4% crosslinked polyacrylamide, and 1% uncrosslinked polyacrylamide molecular weight 700,000–1,000,000 (Polysciences, Inc.). These polymers were added to the carrier ampholyte solution and soaked into the sponge strips overnight. The solution was supplemented with Nonidet P-40 at 1% to facilitate the penetration of polymer into the pores. The crosslinked acrylamide was polymerized and crosslinked into the pores in a horizontal chamber. The polymerization was initiated immediately prior to placing the sponges in the solution and continued overnight.

Zein from corn (Sigma #Z-3625) was conjugated to 5-iodoacetamide fluorescein. The zein was purified by ultrafiltration in a Centricon-10 filter. The resulting protein was run in a 0, 10 or 5% dimethyl formamide/2% carrier ampholyte/1% Nonidet-P40 system in polyethylene 4920 and 4732 sponges to demonstrate that these matrices are compatible with organic solvent based separations.

Standard two dimensional gel electrophoresis was performed as described by Harrington, et al., *Methods: A Companion to Methods in Enzymology*, 1991, 3, 133–139. When the first dimension isoelectric focusing was performed in PVDF or polyethylene sponges, this was achieved on a Pharmacia/LKB FBE-3000 apparatus (as described above) and the strips were transferred to a second dimension SDS-PAGE gel. The second dimension and silver staining protocols were identical to those described in Harrington, et al. Stained gels were digitized on a Molecular Dynamics laser densitometer 300A, raw data was transferred to a Sun 4/260 running GALtool and hard copy images were made on a Lasertechnics (Albuquerque, New Mexico) 300D continuous tone laser printer.

Figure 7:
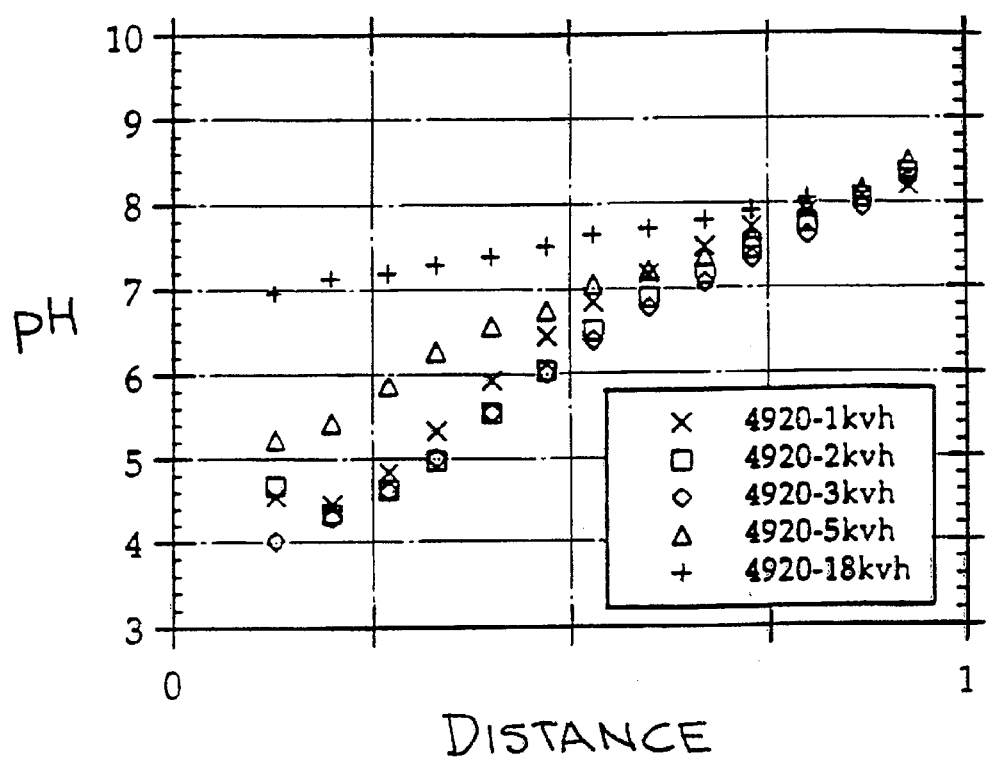
FIG. 7 is a graph of the pH of carrier ampholyte based gradients in polyethylene plotted against the length of the sponge, at different time-points.
Figure 5:
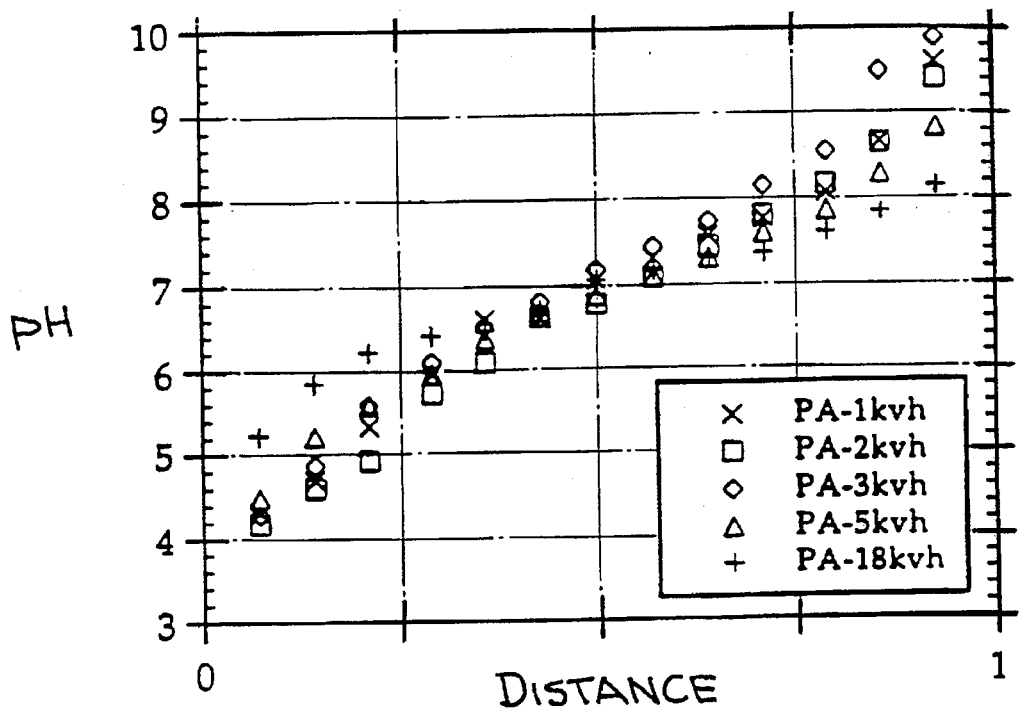
FIG. 5 is a graph of the pH of carrier ampholyte based gradients in polyacrylamide plotted against the length of the gel, at different time-points.
Figure 6:
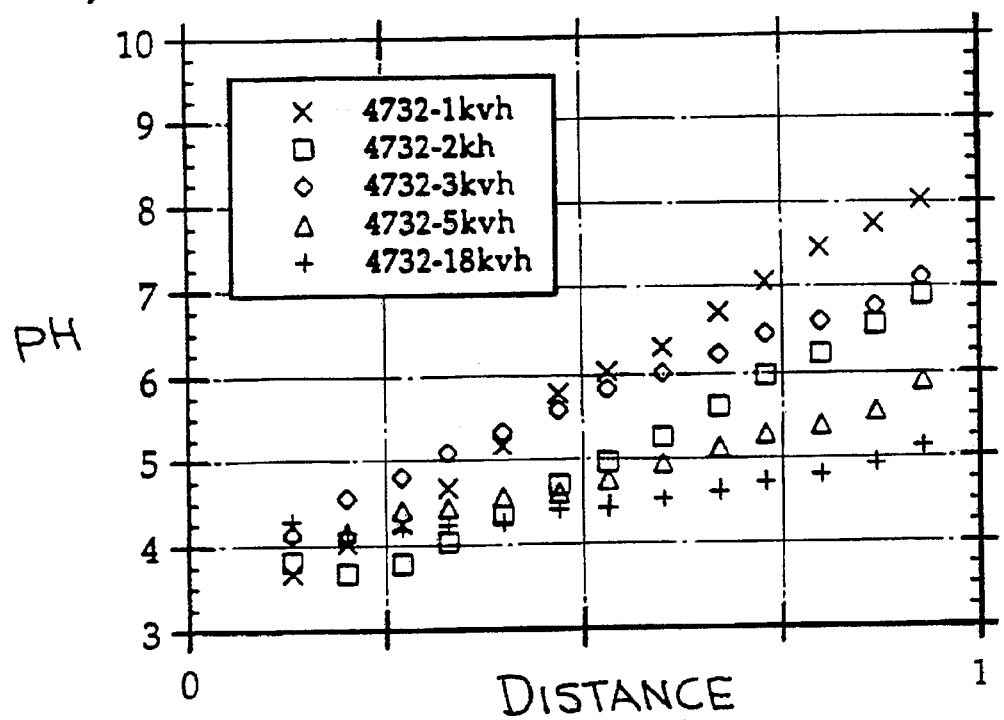
FIG. 6 is a graph of the pH of carrier ampholyte based gradients in PVDF plotted against the length of the sponge, at different time-points.

The pH of carrier ampholyte based gradients in polyacrylamide, PVDF #2732 and polyethylene #4920 were plotted against the length of the media at different time points. Results for polyacrylamide gel are shown in FIG. 5. Results for PVDF #473 and polyethylene #4920 are shown in FIGS. 6 and 7, respectively. As can be seen from FIGS. 5, 6 and 7, good pH gradients are found in two sponges and they have a variety of pH distributions depending on both the running conditions and the type of material.

The two above sponges were found to have greater linearity across their entirety than the polyacrylamide gel gradients at most conditions studied. This is reflected in the linear regression analysis of which was 0.99 for the FIG. 6 and FIG. 7 sponge samples and 0.97 for the FIG. 5 polyacrylamide gel samples. This linearity of the sponge gradients should result in more linear separations than possible by PAGE.

Another feature which was observed during the exemplary electrophoresis runs was that the gradients in polyethylene and PVDF become flatter when IEF is run for progressively longer duration. Those gradients in polyethylene are relatively stable at the basic end, and they become less acute with the change mainly occurring at the acidic end of the strip. The PVDF, on the other hand, has the more stable region at the acidic end, with the flattening of the gradient resulting from changes occurring mainly at the basic end of the strip. The gradient profiles in both of these materials are quite distinct from that in polyacrylamide, and each material can be predicted to have selective advantages. For instance, the greatest separation stability for acidic proteins may be with PVDF sponges, for basic proteins with polyethylene materials, for neutral proteins with polyacrylamide gels. For conducting broad range survey studies, polyethylene sponge is preferred.

The pH graph data (FIGS. 5, 6 and 7) demonstrate that the window of optimal separation in the plastic sponges can vary from broad (4 pH units) to narrow (less than 1 pH unit) over the length of sponge, and across the entire pI range. In contrast to the focusing of basic proteins that can be well achieved with IPG-based polyacrylamide gels, polyacrylamide is notoriously poor for the basic range of proteins with carrier ampholytes. Thus, the polyethylene sponge is a useful medium for IEF with carrier ampholytes in this pI range.

All of the materials and pore sizes listed above were screened for their usefulness as an electrophoresis media. Although all of the porous sponges were found to be suitable, the best results were found with either small pore size "extra fine" polyethylene or the PVDF media. Accordingly, these two types of sponges are preferred.

The radioactively labeled sea urchin embryo proteins focused and, when transferred out of either electrophoresis sponges or polyacrylamide gels, the residual radioactivity in the IEF media was <5%. This demonstrates that with the proteins tested, there was no serious problem caused by proteins sticking to the sponge.

IEF was achieved with these same proteins when any of the added polymers described above were used. No distinct benefit was observed with any of these under the test conditions, but the ability to evaluate the effects of added polymers, solvents or other chemicals is an advantage over polyacrylamide or agarose gels.

The hydrophobic protein zein was focused under both aqueous and 50% dimethylformamide (DMF) conditions and the latter was significantly better in sponges than achieved in polyacrylamide gels. The speed for IEF in the sponges was also found to be on the order of three times faster than the polyacrylamide gel.

As can be seen from the preceding examples, the polymer sponges in accordance with the present invention are well-suited for use in a wide variety of electrophoresis procedures. They differ from electrophoresis gels primarily in that they are mechanically stronger; this gives them the advantage of maintaining a more fixed pore size that does not vary during electrophoresis. They can be handled physically more easily than gels and chemically they can range between hydrophilic or hydrophobic, with inert to reactive surfaces. Pore sizes can range from the sub-nanometer to micron scale.

Hydrophobic sponges in accordance with the present invention are useful for carrier ampholyte-based isoelectric focusing of proteins. Good broad and narrow pH gradients are established in the sponges that are more linear than those achieved with polyacrylamide gels. One and two-dimensional electrophoresis of proteins has also been demonstrated, for example, with high resolution of the charge isomers of haptoglobin beta chain, using sponge-based isoelectric focusing. Focusing is about three-fold faster in the tested sponges than in equivalent polyacrylamide gels, related to the larger sponge pores. Moreover, both the quantity of sample entry of the hydrophobic protein zein and its resolution after isoelectric focusing in the electrophoresis sponges (in the presence of organic solvent) was superior to that achieved in polyacrylamide gels. The electrophoresis sponges of the present invention are therefore suitable alternatives to the existing media used for electrophoresis.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. An electrophoresis support media comprising a polymer sponge having a total sponge volume, said polymer sponge comprising open pores having a pore void volume wherein said open pores define an open pore structure that allows movement of solvents and other materials through said sponge, said pores ranging in size from 0.1 μm to 100 μm meters and wherein the ratio of pore void volume to total sponge volume is between about 40 volume percent to 80 volume percent and wherein said sponge comprises a polymer selected from the group consisting of polyethylene, polypropylene, polytetrafluoroethylene, polyvinylidine difluoride, polynitrile and polystyrene and wherein said polymer sponge comprises at least one well or location which is of suitable size for receiving a sample.

2. An electrophoresis support media according to claim 1 wherein the pores within said polymer sponge have pore sizes which are of sufficient size to allow electrophoretic migration of protein through said polymer sponge during electrophoresis.

3. An electrophoresis support media according to claim 1 wherein the pores within said polymer sponge have pore sizes which are of sufficient size to allow electrophoretic migration of peptides through said polymer sponge during electrophoresis.

4. An electrophoresis support media according to claim 1 wherein the pores within said polymer sponge have pore sizes which are of sufficient size to allow electrophoretic migration of DNA through said polymer sponge during electrophoresis.

5. An electrophoresis support media according to claim 1 wherein said polymer sponge consists essentially of polyvinylidine difluoride.

6. An electrophoresis support media according to claim 1 wherein said polymer sponge consists essentially of polyethylene.

7. An electrophoresis system comprising:

a polymer sponge having a total sponge volume, said polymer sponge comprising open pores having a pore void volume wherein said open pores define an open pore structure that allows movement of solvents and other materials through said sponge, said pores ranging in size from 0.1 μm to 100 μm meters and wherein the ratio of pore void volume to total sponge volume is between about 40 volume percent to 80 volume percent and wherein said sponge comprises a polymer selected from the group consisting of polyethylene, polypropylene, polytetrafluoroethylene, polyvinylidine difluoride, polynitrile and polystyrene and wherein said polymer sponge comprises at least one well or location which is of suitable size for receiving a sample; and an electrophoresis solvent dispersed within said polymer sponge.

8. An electrophoresis system according to claim 7 wherein said solvent is an organic solvent.

9. An electrophoresis system according to claim 7 for separating proteins wherein the pores within said polymer sponge have pore sizes which are of sufficient size to allow electrophoretic migration of said proteins through said polymer sponge during electrophoresis.

10. An electrophoresis system according to claim 7 for separating peptides wherein the pores within said polymer sponge have pore sizes which are of sufficient size to allow electrophoretic migration of peptides through said polymer sponge during electrophoresis.

11. An electrophoresis system according to claim 7 for separating DNA wherein the pores within said polymer sponge have pore sizes which are of sufficient size to allow electrophoretic migration of DNA through said polymer sponge during electrophoresis.

12. An electrophoresis system according to claim 7 wherein said polymer sponge consists essentially of polyvinylidine difluoride.

13. An electrophoresis system according to claim 7 wherein said polymer sponge consists essentially of polyethylene.

* * * * *